(12) United States Patent
Dhawan et al.

(10) Patent No.: US 12,029,814 B1
(45) Date of Patent: Jul. 9, 2024

(54) FORMULATION OF EAR DROPS AND METHODS FOR DELIVERY THEREOF FOR TREATING UPPER RESPIRATORY INFECTIONS

(71) Applicants: Subhash Dhawan, Gaithersburg, MD (US); Yashi Dhawan, Lucknow (IN)

(72) Inventors: Subhash Dhawan, Gaithersburg, MD (US); Yashi Dhawan, Lucknow (IN)

(73) Assignees: Subhash Dhawan, Gaithersburg, MD (US); Yashi Dhawan, Lucknow (IN)

( * ) Notice: Subject to any disclaimer, the term of this patent is extended or adjusted under 35 U.S.C. 154(b) by 0 days.

(21) Appl. No.: 18/488,942

(22) Filed: Oct. 17, 2023

Related U.S. Application Data

(60) Provisional application No. 63/542,320, filed on Oct. 4, 2023.

(51) Int. Cl.
| | |
|---|---|
| *A61K 9/00* | (2006.01) |
| *A61K 9/127* | (2006.01) |
| *A61K 31/409* | (2006.01) |
| *A61K 31/675* | (2006.01) |
| *A61N 1/36* | (2006.01) |
| *A61P 31/14* | (2006.01) |

(52) U.S. Cl.
CPC ............ *A61K 9/0046* (2013.01); *A61K 9/127* (2013.01); *A61K 31/409* (2013.01); *A61K 31/675* (2013.01); *A61N 1/36036* (2017.08); *A61P 31/14* (2018.01)

(58) Field of Classification Search
None
See application file for complete search history.

(56) References Cited

U.S. PATENT DOCUMENTS

| | | | |
|---|---|---|---|
| 11,724,077 B2 | 8/2023 | Dhawan | |
| 2016/0022666 A1* | 1/2016 | Yaacobi | A61K 31/4709 514/300 |
| 2020/0397711 A1* | 12/2020 | Lee | A61K 9/127 |
| 2023/0270756 A1* | 8/2023 | Kameswari | A61K 9/1271 424/450 |
| 2023/0364188 A1* | 11/2023 | Osada | A61K 9/0046 |

FOREIGN PATENT DOCUMENTS

WO    WO-2021195765 A1 * 10/2021 ............. A61K 31/10

OTHER PUBLICATIONS

Kim et al (Scientific Reports, 2021, 11:21462, 1-9). (Year: 2021).*
Health Desk (Year: 2021).*
Chi X, Guo N, Yao W, Jin Y, Gao W, Cai J, Hei Z. Induction of heme oxygenase-1 by hemin protects lung against orthotopic autologous liver transplantation-induced acute lung injury in rats. J Transl Med. Feb. 2, 2016;14:35. doi: 10.1186/s12967-016-0793-0. PMID: 26838179; PMCID: PMC4736160.
Clement A. Meseda, Kumar Srinivasan, Jasen Wise, Jennifer Catalano, Kenneth M. Yamada, Subhash Dhawan, Non-coding RNAs and heme oxygenase-1 in vaccinia virus infection, Biochemical and Biophysical Research Communications, vol. 454, Issue 1, 2014, pp. 84-88.
Devadas, Krishnakumar, and Subhash Dhawan. "Hemin activation ameliorates HIV-1 infection via heme oxygenase-1 induction." The Journal of Immunology 176, No. 7 (2006): 4252-4257.
Dhawan S. Therapeutic Potential of Inducible Endogenous Cytoprotective Heme Oxygenase-1 in Mitigating SARS-CoV-2 Infection and Associated Inflammation. Antioxidants. 2022; 11(4):662. https://doi.org/10.3390/antiox11040662.
Dhawan, S. "Significance of Innate Immunity in Mitigating SARS-CoV-2 Infection" Dhawan, S. Am. Pharm. Rev. 48-49 (May/Jun. 2021).
Dhawan, S. "Therapeutic potential of endogenous heme oxygenase-1 activation in pathogenic infections." Curr. Trends Immunol. 14:65-70 (2013).
Dhawan, S. Curr. "Necessity for the evaluation of stimulated cellular immunity against SARS-CoV-2 infection" Trends Immunol. 22:43-47 (2021).
Hill-Batorski et al. "The Cytoprotective Enzyme Heme Oxygenase-1 Suppresses Ebola Virus Replication", J. Virol. 87:13795-13802 (2013).
Huang et al. "Hemin activation abrogates Mycoplasma hyorhinis replication in chronically infected prostate cancer cells via heme oxygenase-1 induction" FEBS Open Bio. Published online on Aug. 10, 2021; https://doi.org/10.1002/2211-5463.13271.
Huang H, Falgout B, Takeda K, Yamada KM, Dhawan S. "Nrf2-dependent induction of innate host defense via heme oxygenase-1 inhibits Zika virus replication." Virology. Mar. 2017;503:1-5. doi: 10.1016/j.virol.2016.12.019. Epub Jan. 6, 2017. PMID: 28068513; PMCID: PMC5325777.
Huang H, Konduru K, Solovena V, Zhou ZH, Kumari N, Takeda K, Nekhai S, Bavari S, Kaplan GG, Yamada KM, Dhawan S. "Therapeutic potential of the heme oxygenase-1 inducer hemin against Ebola virus infection." Curr Trends Immunol. 2016;17:117-123. PMID: 28133423; PMCID: PMC5267496.

(Continued)

*Primary Examiner* — Celeste A Roney
(74) *Attorney, Agent, or Firm* — Knobbe, Martens, Olson & Bear, LLP

(57) ABSTRACT

Compound formulations and methods for preventing or treating upper respiratory virus infections, such as influenza, respiratory syncytia virus (RSV), SARS, and SARS-COV-2, in human and animal species are disclosed. The compounds may exhibit antiviral, antimicrobial, anti-inflammatory, or cytoprotective activities. Liquid formulations comprising one or more compounds may be administered into the outer canal of the ear for delivery to the nasal and oral cavities, nasopharynx, posterior pharynx and laryngopharynx, the primary sites of upper respiratory infections, located across the tympanic membrane (or eardrum) and eustachian tube, of the individuals infected with one or more upper respiratory viruses or other pathogens. Methods to facilitate trans-tympanic membrane translocation of the compounds by thermal, electrical or electromagnetic impulse, manual or mechanical muscle contraction or stimulation of muscles, nerves or tissues proximate to the eardrum are disclosed.

18 Claims, 5 Drawing Sheets

(56) References Cited

OTHER PUBLICATIONS

Rossi M, Piagnerelli M, Van Meerhaeghe A, Zouaoui Boudjeltia K. Heme oxygenase-1 (HO-1) cytoprotective pathway: A potential treatment strategy against coronavirus disease 2019 (COVID-19)-induced cytokine storm syndrome. Med Hypotheses. Nov. 2020;144:110242. doi: 10.1016/j.mehy.2020.110242. Epub Sep. 3, 2020. PMID: 33254548; PMCID: PMC7467863.

Wagener, F.A.D.T.G.; Pickkers, P.; Peterson, S.J.; Immenschuh, S.; Abraham, N.G. Targeting the Heme-Heme Oxygenase System to Prevent Severe Complications Following COVID-19 Infections. Antioxidants 2020, 9, 540. https://doi.org/10.3390/antiox9060540.

Zhou ZH, Kumari N, Catalano J, Nekhai S, Wise J, Yamada KM, Dhawan S. "Heme oxygenase-1-mediated host cell response inhibits the susceptibility of prostate cancer cells to retroviral infection and retards their proliferation." Curr Trends Immunol. Jan. 2013;14:53-56. PMID: 25620854; PMCID: PMC4302767.

Zhang et al., "Drug Delivery across Barriers to the Middle and Inner Ear." Adv Funct Mater. Oct. 26, 2021;31(44):2008701.

Dapsone—Uses, Side Effects, and More https://www.webmd.com/drugs/2/drug-6744/dapsone-oral/details.

\* cited by examiner

Figure 1

Delivery of antiviral drugs across tympanic membrane to primary sites of upper respiratory infections

Figure 3

Dose response curve of hemin against SARS-CoV-2 Omicron BA.1

● Omicron MOI = 0.01
□ Omicron MOI = 0.001

IC50 Omicron (MOI 0.01) = 5.374
$R^2$ = 0.829 (pretty good fit)
IC50 Omicron (MOI 0.001) = 6.751
$R^2$ = 0.685 (mediocre fit)

FORMULATION OF EAR DROPS AND METHODS FOR DELIVERY THEREOF FOR TREATING UPPER RESPIRATORY INFECTIONS

INCORPORATION BY REFERENCE TO ANY PRIORITY APPLICATIONS

This application claims the priority benefit of U.S. Provisional Patent Application No. 63/542,320, filed Oct. 4, 2023, titled "FORMULATION OF EAR DROPS AND METHODS FOR DELIVERY THEREOF FOR TREATING UPPER RESPIRATORY INFECTIONS", the entirety of which is incorporated by reference herein.

Any and all applications for which a foreign or domestic priority claim is identified in the Application Data Sheet as filed with the present application are hereby incorporated by reference under 37 CFR 1.57.

BACKGROUND

Technical Field

The field relates to treatment of upper respiratory infections, and in particular to treatment of upper respiratory infections by means of targeted application of therapeutics to the site of infection.

Description of the Related Art

Infections caused by upper respiratory viruses, including influenza, respiratory syncytia virus (RSV) SARS, and novel strains of COVID-19-causing coronavirus SARS-COV-2 and its mutant variant strains are transmissible in proximity. Upper respiratory virus may trigger respiratory illnesses and serious health complications. Although vaccines show effectiveness in reducing the severity of COVID-19 illnesses, hospitalizations and deaths, none is yet known to prevent infections or reinfections of the vaccinated individuals by rapidly emerging highly contagious and more deadly mutant viral variants. In addition, children, older population, and individuals with underlying health conditions, all are at a significantly higher risk of acquiring the infection and developing hyperinflammatory syndrome and other severe health complications. Therapeutic options for treating infections with viruses such as SARS-COV-2, influenza and RSV are limited and often require hospitalizations. The dire current COVID-19 pandemic situation calls for an urgent need for safe and effective therapeutics to treat the infected individuals.

SUMMARY

In some aspects, disclosed herein are therapeutic formulations of compounds and use thereof in a method for treating upper respiratory infections in a subject.

In a first aspect, disclosed herein are otic applications. In some embodiments, the otic applications comprise at least one carrier medium, and at least one antiviral agent. In some embodiments, the otic application is configured for use in an ear of a human or animal subject for preventing, reducing, or treating upper respiratory infections. In some embodiments, the otic application is configured to transport across a tympanic membrane of the subject from the ear. In some embodiments, the otic application may include one of more compounds having a property of: an antiviral agent, a heme oxygenase-1 (HO-1) modulator, a drug component having anti-inflammatory activity; and/or a drug component having cytoprotective activity. In some embodiments, the active ingredient comprises hemin, remdesivir, or a combination thereof. In some embodiments, the upper respiratory infection is SARS-COV-2.

In some embodiments, the otic application is liquid. In some embodiments, the otic application includes a fragrant essential oil, which in some embodiments may be used by the subject's olfactory senses to detect whether the otic application has reached the upper respiratory system from the ear. In some embodiments, the carrier medium includes drug-loaded nanoparticles. In some embodiments, the carrier medium includes drug-loaded lipid vesicles. In some embodiments, the otic application includes a lubricant. In some embodiments, the otic application is substantially free of irritants.

In a second aspect, disclosed herein are otic applications. In some embodiments, the otic applications comprise at least one carrier medium, and at least one heme oxygenase-1 (HO-1) modulator. In some embodiments, the otic application is configured for use in an ear of a human or animal subject for preventing, reducing, or treating upper respiratory infections.

In a third aspect, disclosed herein are otic applications. In some embodiments, the otic applications comprise at least one carrier medium, and at least one drug having cytoprotective activity. In some embodiments, the otic application is configured for use in an car of a human or animal subject for preventing, reducing, or treating upper respiratory infections.

In a further aspect, disclosed herein are methods for treating upper respiratory infections in a human or animal subject. In some embodiments, the method includes identifying a subject having a upper respiratory infection and administering a drug formulation to the ear of the subject. The drug formulation may include at least one antiviral agent and at least one carrier medium. In some embodiments, the drug formulation may include one of more compounds having a property of: an antiviral agent, a heme oxygenase-1 (HO-1) modulator, a drug component having anti-inflammatory activity; and/or a drug component having cytoprotective activity. In some embodiments, the drug formulation includes a fragrant essential oil. That essential oil may be used to detect whether the drug formulation has been delivered into an upper respiratory system of the subject by detecting the scent of the fragrant essential oil by olfactory tissues, according to certain embodiments. The fragrant essential oil may also be included for its therapeutic effects.

In some embodiments, the antiviral agent may include hemin, remdesivir, or a combination of the two. In some embodiments, the drug formulation may be administered repeatedly over a time period, such as administering at least twice a day for three days to suppress infections at primary sites of upper respiratory infection and to reduce viral-associated clinical symptoms. The method may include applying thermal, electrical or electromagnetic impulse, manual or mechanical muscle contraction or stimulation of muscles, nerves or tissues externally proximate to an eardrum to facilitate drug absorption and translocation of drugs across a tympanic membrane of the subject. In some embodiments, this application of thermal, electrical or electromagnetic impulse, manual or mechanical muscle contraction or stimulation of muscles, nerves or tissues externally proximate to an eardrum may be accomplished by use of a device applying transcutaneous electrical nerve stimulation externally proximate to the eardrum.

BRIEF DESCRIPTION OF THE DRAWINGS

Features of examples of the present disclosure will become apparent by reference to the following detailed description and drawings, in which like reference numerals correspond to similar, though perhaps not identical, components. For the sake of brevity, reference numerals or features having a previously described function may or may not be described in connection with other drawings in which they appear. In addition to the features described herein, additional features and variations will be readily apparent from the following descriptions of the drawings and exemplary embodiments. It is to be understood that these drawings depict typical embodiments, and are not intended to be limiting in scope.

FIG. 1 illustrates a delivery of therapeutics to the upper respiratory system via the car canal and eustachian tube, according to certain embodiments.

FIG. 3 depicts a dose response curve of hemin against SARS-COV-2, according to certain embodiments.

DETAILED DESCRIPTION

Figure 2:
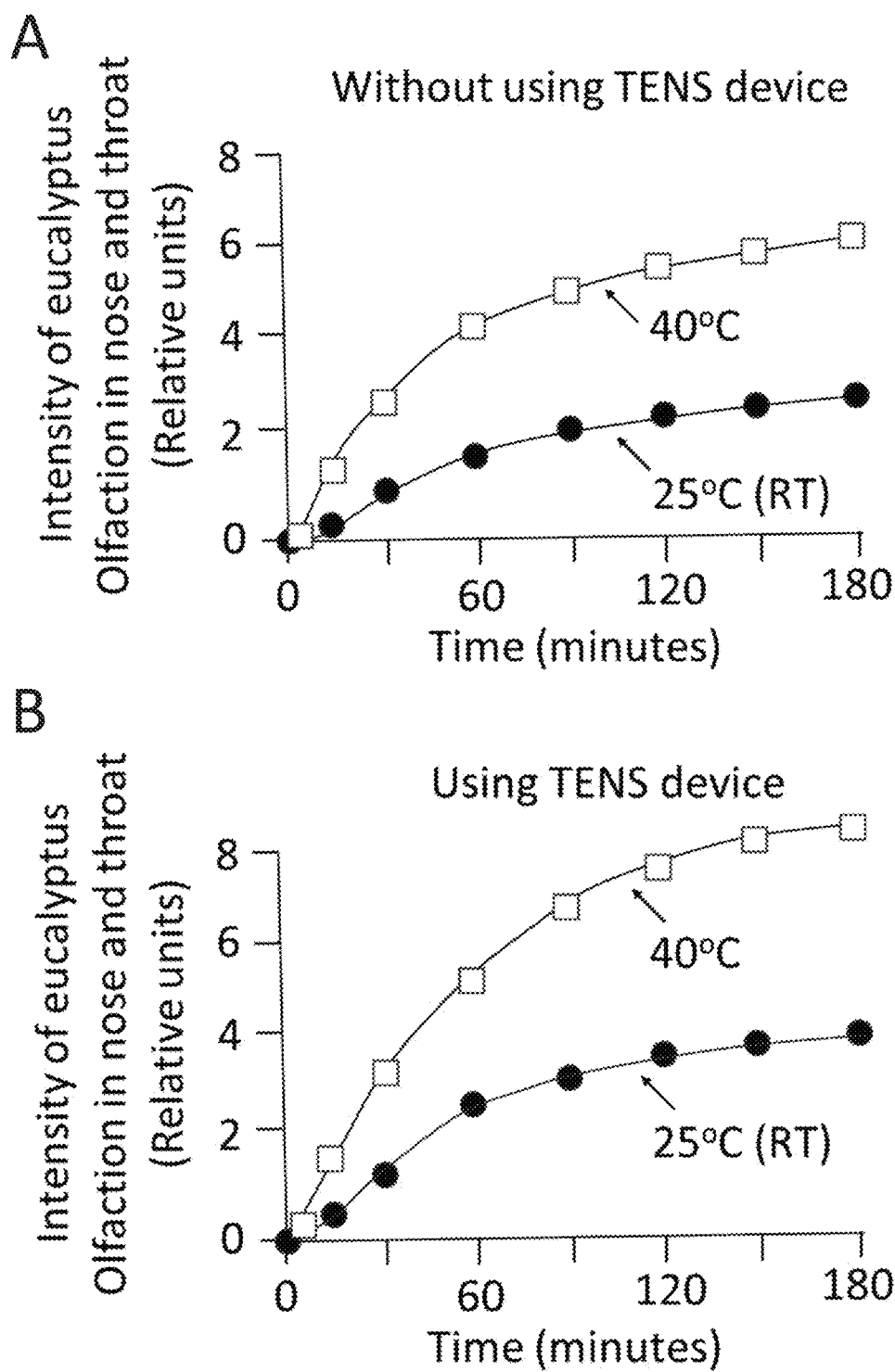
FIG. 2 depicts line graphs illustrating the effects of TENS device usage and liquid otic application temperature on carrier oil permeation across the tymphanic membrane, according to certain embodiments.

The foregoing and other aspects of the present disclosure will now be described in more detail with respect to the description and methodologies provided herein. This description is not intended to be a detailed catalogue of all the ways in which the embodiments of the present disclosure may be implemented, or of all the features that may be added to the present disclosure. For example, features illustrated with respect to one embodiment may be incorporated into other embodiments, and features illustrated with respect to a particular embodiment may be deleted from that embodiment. In addition, numerous variations and additions to the various embodiments suggested herein, which do not depart from the instant disclosure, will be apparent to those skilled in the art in light of the instant detailed description, figures and claims. Hence, the following specification is intended to illustrate some particular embodiments, and not to exhaustively specify all permutations, combinations and variations thereof.

All patents, patent applications, and other publications, including all sequences disclosed within these references, referred to herein are expressly incorporated herein by reference, to the same extent as if each individual publication, patent or patent application was specifically and individually indicated to be incorporated by reference. All documents cited are, in relevant part, incorporated herein by reference in their entireties for the purposes indicated by the context of their citation herein. However, the citation of any document is not to be construed as an admission that it is prior art with respect to the present disclosure.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Definitions

Although the following terms are believed to be well understood by one of skill in the art, the following definitions are set forth to facilitate understanding of the presently disclosed subject matter.

All technical and scientific terms used herein, unless otherwise defined below, are intended to have the same meaning as commonly understood by one of ordinary skill in the art. References to techniques employed herein are intended to refer to the techniques as commonly understood in the art, including variations on those techniques or substitutions of equivalent techniques that would be apparent to one of skill in the art.

As used herein, the terms "a" or "an" or "the" may refer to one or more than one. For example, "a" marker can mean one marker or a plurality of markers.

As used herein, the term "about," when used in reference to a measurable value such as an amount of mass, dose, time, temperature, and the like, is meant to encompass variations of 20%, 10%, 5%, 1%, 0.5%, or even 0.1% of the specified amount.

As used herein, the term "and/or" refers to and encompasses any and all possible combinations of one or more of the associated listed items, as well as the lack of combinations when interpreted in the alternative ("or").

Throughout this specification, unless the context requires otherwise, the words "comprise," "comprises," and "comprising" will be understood to imply the inclusion of a stated step or element or group of steps or elements but not the exclusion of any other step or element or group of steps or elements.

As used herein, the term "consists essentially of" (and grammatical variants thereof), as applied to the compositions and methods of the present disclosure, means that the compositions/methods may contain additional components so long as the additional components do not materially alter the composition/method. The term "materially alter," as applied to a composition/method, refers to an increase or decrease in the effectiveness of the composition/method of at least about 20% or more. For example, a component added to a composition of the present disclosure would "materially alter" the composition if it increases or decreases the composition's ability to inhibit tumor growth by at least 20%.

A "carrier medium" should be interpreted as would be understood by a person having skill in the art but also refers to a substance or material used to transport and deliver therapeutic compounds from their point of application to target sites within the body.

"Antiviral agent" should be interpreted as would be understood by a person having skill in the art but also refers to a compound that interferes with virus life cycle, prevents its replication, or directly eliminates viruses. In other words, an antiviral agent is a compound possessing antiviral activity that inhibits viral replication or infection. For example, an antiviral agent may target a viral protein or part of a viral protein and disable it.

"Heme oxygenase-1 (HO-1) modulator" should be interpreted as would be understood by a person having skill in the art but also refers to a substance or agent that significantly influences the activity or expression of heme oxygenase-1.

"Cytoprotective activity" should be interpreted as would be understood by a person having skill in the art but also refers to protecting or preserving the structural and functional integrity of cells against harmful or damaging effects of viral infection.

Overview

The present disclosure is directed to compounds and methods for preventing or treating upper respiratory virus infections. Current therapeutic options for treating COVID-19 and other upper respiratory infections in patients are limited and may require hospitalization. In addition to vaccines development against SARS-COV-2, the current pandemic situation that is worsened by constantly emerging deadly mutant viral strains, calls for an urgent need for safe and effective therapeutics to treat the infected individuals at the early symptomatic stage of infection. In addition, convenient self-administering approaches are much needed to reduce the severity and to minimize the spread of infections to others.

Accordingly, the present disclosure addresses this public health emergency, in part, and presents evidence for cellular protection against all thus far identified variants of SARS-COV-2 by drugs exhibiting antiviral, anti-inflammatory, and cytoprotective characteristics. This disclosure also presents evidence for reducing viral infection and virus-associated symptoms in a subject tested for COVID-19 by intra-ear administration of a drug. The intra-ear administration of one or more drugs formulated in a proper drug-carrying media, such as oils, and delivery thereof across the eustachian tube (or ear drum) in the middle car that directly connects tympanic membrane of the outer ear to nasopharynx, posterior pharynx, oropharynx and laryngopharynx, the primary sites of upper respiratory infections, are disclosed. The use of transcutaneous electric nerve stimulation (TENS) device or electrical/mechanical agitation device placed externally proximate to the tympanic membrane (or eardrum) to facilitate translocation of drug across the tympanic membrane is disclosed. Collectively, these disclosures provide a novel therapeutic approach for treating upper respiratory infections.

Respiratory viruses, including SARS-COV-2, enter through nose and mouth and infect nasopharynx, posterior pharynx, laryngopharynx, the primary sites of upper respiratory infection, located at the back of the nose and throat. These infection sites are connected to eustachian tube in the middle ear that separates the outer car canal by tympanic membrane as shown in FIG. 1. Due to hydrophobicity of the tympanic membrane and lack of proper and safe chemical compositions of drugs-carrying media, transport of antiviral drugs across the tympanic membrane to efficiently treat upper respiratory infections, including COVID-19, is unknown in the art.

A patent entitled "THERAPEUTIC SWABS FOR TREATING UPPER RESPIRATORY INFECTIONS" (U.S. Pat. No. 11,724,077) was recently issued to one of the inventors, Subhash Dhawan, and relates to treatment of upper respiratory infection by use of a therapeutic swab configured to deliver therapeutic compounds to sites of infection. That issued patent is hereby incorporated by reference. While the approach presented in the issued patent is novel for treating upper respiratory infections, disclosed herein are several major improvements over the previously approved patent by the inventor in many aspects. Among other things, the present disclosure discloses: (a) direct drug delivery to the same primary sites of upper respiratory infections as reported in the previous patent, without the need for insertion of a drug-loaded swab through the nostrils of a subject, according to certain embodiments; (b) methods to facilitate trans-tympanic membrane translocation of the compounds by thermal, electrical or electromagnetic impulse, manual or mechanical muscle contraction or stimulation of muscles, nerves or tissues proximate to the tympanic membrane (or eardrum), according to certain embodiments; (c) quicker and easier methods of self-administration of drug(s) by a subject with or without to a professional assistance, according to certain embodiments; (d) treatments that are substantially cost-effective and easy to manufacture, according to certain embodiments; (e) a treatment kit to be used by medical professionals or by end users; (f) treatments that can be used at a mass-scale to control COVID-19 and other respiratory viral endemics or pandemics, according to certain embodiments.

Certain embodiments may demonstrate cellular protection against all thus far identified all mutant variants of SARS-COV-2, including the newly identified strains XBB and XBB1.5, by tympanic membrane delivery of antiviral drugs such as hemin and remdesivir (RMD), chosen in this disclosure as examples for other antiviral drugs. The two drugs work in different ways. Hemin inhibits a variety of infections via the induction of a host protective endogenous enzyme heme oxygenase-1 (HO-1) (Devadas, K. & Dhawan, S. J. Immunol 176:4252-4257 (2006); Zhou et al. Curr. Trends Immunol. 14:53-56 (2013); Dhawan, S. Curr. Trends Immunol. 14:65-70 (2013); Meseda et al. Biochem. Biophys. Res. Commun. 454:84-88 (2014); Huang et al. Curr. Trends Immunol. 17:117-123 (2016); Hill-Batorski et al. J. Virol. 87:13795-13802 (2013); Huang et al. Virology. 503: 1-5 (2017); Chi et al. J. Transl. Med. 14:35 (2016); Wagener et al. Antioxidants. 9:540 (2020); Chi et al. J. Transl. Med. 14:35 (2016); Rossi et al. Med. Hypothesis. 144:110242 (2020); Huang et al. FEBS Open Bio. Published online on Aug. 10, 2021; https://doi.org/10.1002/2211-5463.13271; Dhawan, S. Curr. Trends Immunol. 22:19-21 (2021); Dhawan, S. Curr. Trends Immunol. 22:43-47 (2021); Dhawan, S. Am. Pharm. Rev. 48-49 (May/June 2021), all herein incorporated by reference). RMD suppresses viral infections by a mechanism that involves targeting RNA-dependent polymerase which is an essential enzyme for viral replication. Therefore, the use of HO-1-inducing compounds as cytoprotective factors along with other antiviral drugs either individually or in combinations could be ideal candidates for successfully treating upper respiratory viral infections.

The present disclosure proposes the use of one drug or combination of drugs individually or simultaneously that may be delivered through the car to the infected sites of upper respiratory infections. Accordingly, the present disclosure includes selection of compounds possessing: (a) antiviral activity to disrupt the viruses or inhibit viral replication; (b) anti-inflammatory activity to reduce inflammation associated with viral infections; and (c) cytoprotective function to prevent virus-induced cell death and to protect the target cells from being infected to collectively combat infections and to provide an effective host protection.

The present disclosure also includes formulations of drug-carrier media in certain conditions to facilitate its absorption and transport across the tympanic membrane to deliver drugs to the primary sites of upper respiratory infections under various conditions here described. In addition, this disclosure includes a new treatment of COVID-19, rendered by placing a few drops of a drug-containing formulation into the outer ear canal of a subject tested positive for COVID-19. A detailed description on the above is provided in the later paragraphs of this disclosure.

To make a person with ordinary skill of the art clearly understand the present disclosure, it is important to be familiarized with specific areas that are affected by upper respiratory infections, which are illustrated in FIG. 1 and further described below. In one aspect, the present disclosure relates to formulations of one or more drugs and delivery thereof to the primary sites of upper respiratory infections, including COVID-19. In another aspect, the present disclosure provides a new approach for the delivery of antiviral drugs administered in the ear to the target sites nasopharynx, oropharynx, posterior pharynx and laryngopharynx located at the end of the eustachian tube. As will be familiar to those skilled in the art, systemic administration of drugs either orally, by injections, or via other routes is not without the risk of causing adverse effects, sometimes serious in nature. Therefore, certain embodiments contemplate delivery of one or more drugs exhibiting antiviral, antimicrobial or cytoprotective functions for efficient targeting of the primary infection sites nasopharynx, posterior pharynx, laryngopharynx across the tympanic membrane.

FIG. 1 illustrates the anatomy of the human upper respiratory system and human auditory system. The nasopharynx, oropharynx and laryngopharynx are parts of the human upper respiratory system, and are located at the far back of the nasal cavity behind the human face and above the oral cavity as shown in FIG. 1. The human ear is disposed on the side of the head and comprises an outer ear canal in a recess of the ear. The upper respiratory system and the outer ear are connected by a passage through the tympanic membrane (commonly known as the eardrum), then through middle ear, and then the eustachian tube past the middle ear as shown in the figure. At the anterior end of the passageway, the eustachian tube connects with the upper respiratory system at the orifice of the eustachian tube, which is disposed near the nasopharynx, oropharynx, and laryngopharynx.

The nasopharynx, oropharynx, and laryngopharynx are primary sites of upper respiratory infections. As illustrated in FIG. 1, the human ear is relatively close in distance to the laryngopharynx, the oropharynx, and the nasopharynx. Because of this short distance, a therapeutic compound which can transport across the tympanic membrane, may allow rapid drug delivery to these sites in an effective manner. FIG. 1 illustrates delivery of antiviral drugs to the laryngopharynx, the oropharynx, and the nasopharynx according to certain embodiments. Antiviral drugs are introduced into the outer ear canal, from where they transport across the tympanic membrane and pass into the middle ear. The antiviral drugs then pass through the eustachian tube and then enter the upper respiratory system, where they can interact with the laryngopharynx, the oropharynx, and the nasopharynx. Because the nasopharynx, oropharynx, posterior pharynx and laryngopharynx are located in the close vicinity of the eustachian tube, certain embodiments presents a therapeutic modality to provide effective treatment of COVID-19- or other respiratory diseases in virus-infected individuals.

This disclosure presents a tremendous superiority over the antiviral or antimicrobial drug administrations by nasal drops or nasal sprays in terms of minimizing the dripping or spilling of the drugs and/or contaminated nasal secretions, signifying a broader public health utility of the present disclosure. The approach presented herein not only has the potential to effectively treat upper respiratory infections, but it can also minimize the risk of adverse side effects associated with high systemic absorption of drugs that are administered in the form of oral medicines or injections, according to certain embodiments. The therapeutic approach presented in this disclosure is much warranted to control the current out-of-control COVID-19 pandemic and also for treating other respiratory viral infections such as RSV, the virus that predominantly infects adults over 60 years of age, and influenza, according to certain embodiments.

The utility of the present disclosure will have a tremendous positive impact on the public health safety on a mass-scale in controlling the current constantly reemerging COVID-19 pandemic crisis as well as in preparing us for the unforeseen future viral outbreaks. This disclosure presents a convenient, useful and practical therapeutic tool to offer medical interventions by healthcare professionals, by other individuals, by friends and family members, by self-administration, for travelers, or for home use to minimize the spread of deadly respiratory infections to others and to retard the disease progression, according to certain embodiments. The present disclosure has a tremendous potential for its utility as a safeguard for preventing or treating upper respiratory infections caused by current and future viral outbreaks.

Formulations

In some aspects, the techniques described herein relate to an otic application, including at least one carrier medium and at least one antiviral agent. wherein the otic application is configured for use in an ear of a human or animal subject for preventing, reducing, or treating upper respiratory infections such as SARS-COV-2.

A drug or combination of drugs formulated in a proper liquid medium may diffuse or permeate through the tympanic membrane. A few drops of this mixture, placed in the outer ear, can be delivered to the primary sites of upper respiratory infections. In certain embodiments, formulations may include drug-loaded nanoparticles. In certain embodiments, a drug encapsulated in lipid vesicles (liposomes), etc., may be used.

In some embodiments, the otic application comprises at least one antiviral agent. Antiviral agents may include compounds that interfere with the lifecycle of a virus, prevent its replication, or directly eliminate the virus, and may thereby reduce the severity and duration of viral infections and prevent their spread when the agents are present at the site of infection. Antiviral agents may work by inhibiting viral replication by blocking entry into host cells, blocking genome replication, or inhibiting the release of newly formed virus particles. Some antiviral agents interfere with viral enzymes essential for replication, while others physically destroy viral particles. In some embodiments, the antiviral agent comprises antiviral drug hemin, which inhibits a variety of infections via the induction of a host protective endogenous enzyme heme oxygenase-1 (HO-1). In some embodiments, the antiviral agent comprises remdesivir (RMD). Without being bound by theory, RMD may suppress viral infections by a mechanism that involves targeting RNA-dependent polymerase which is an essential enzyme for viral replication. In some embodiments, the antiviral agent may be a protein, a peptide, a peptidomimetic, and/or a modified heparin. In some embodiments, the antiviral agent may treat upper respiratory infections of SARS-COV-2, the viral cause of a worldwide pandemic.

In some embodiments, the otic application comprises at least one heme oxygenase-1 (HO-1) modulator. In some embodiments, the at least one heme oxygenase-1 (HO-1) modulator comprises hemin, which causes induction of a host protective endogenous enzyme heme oxygenase-1 (HO-1).

In some embodiments, the otic application comprises at least one drug component having anti-inflammatory activity. In some embodiments, the at least one drug component having anti-inflammatory activity comprises corticosteroids, salicyclates, and/or curcumin. In some embodiments, the drug component having anti-inflammatory may reduce inflammation of the upper respiratory system that results from viral infection.

In some embodiments, the otic application comprises at least one drug component having cytoprotective activity. The cytoprotective activity can manifest in several ways, including reducing oxidative stress, enhancing cellular repair mechanisms, strengthening cell membranes, and reducing harmful inflammation. In some embodiments, the at least one drug component having cytoprotective activity comprises hemin, a strong inducer of an endogenous cytoprotective enzyme heme oxygenase-1 (HO-1).

In some embodiments, the application comprises at least one carrier medium. In certain embodiments, small drug molecules are formulated in a carrier medium, preferably non-polar media (for example, oils or other drug carriers) with compatibility to the lipid-rich hydrophobic tympanic membrane that could promote translocation of drugs across the tympanic membrane via diffusion, active or passive transport, or permeation.

Mineral oils, essential oils and non-essential oils are widely used in skin care products, cosmetics and for body massage because of their nourishment values and permeability across the skin to maintain moisture in the body parts. It was tested whether these oils could transport through the tympanic membrane to the upper respiratory system, as described in the examples below. In some embodiments, the carrier medium may comprise drug-loaded nanoparticles containing the antiviral agent and/or other drug components. In some embodiments, the carrier medium may comprise drug-loaded lipid vesicles containing the antiviral agent and/or other drug components. The drug-loaded nanoparticles or the drug-loaded lipid vesicles contain the antiviral agents or drug components and allow for transportation through the tympanic membrane and down the eustachian tube by shielding the antiviral agents or drug components from unnecessarily high interaction with the tympanic membrane or eustachian tube walls. In certain embodiments, the carrier medium is a liquid that creates a flow from the outer ear canal where the otic application is placed through the tympanic membrane and down the eustachian tube such that the antiviral agents or drug components are transported, carried along on the flow to the upper respiratory system.

In some embodiments, the otic application is configured to transport across a tympanic membrane of the subject from the ear. This configuration may lead to a carrier medium of the correct polarity to transport the drug components and/or antiviral agents it carries. It may also lead to a carrier medium, drug components, and antiviral agents of sufficiently small size to transport across or permeate the porous tympanic membrane porous (about 100-150 μm).

In certain embodiments, some otic application formulations may lubricate the eustachian tube to repel backflow of the fluids from back of the nose and throat to the middle ear in most viral infections. Accordingly, in some embodiments, the otic application may comprise a lubricant. In certain embodiments, some otic application formulations may be free of irritants such that the user will not experience any noticeable adverse effects on the inner ear or on the sense of hearing.

In some embodiments, a fragrant essential oil may be included in the carrier medium or in the otic application. Fragrant essential oils are widely held to have therapeutic properties to assist the ill subject. Further, essential oils may have a beneficial polarity for transporting other therapeutics as a carrier medium. Finally, fragrant essential oils may allow the subject to detect the arrival of the drug formulation from its application in the ear to the upper respiratory system when the characteristically-pleasing scents of the fragrant essential oils are detected in the nose, just above the nasopharynx where the Eustachian tube connects.

In some aspects, the techniques described herein relate to an otic application, including at least one carrier medium and at least one heme oxygenase-1 (HO-1) modulator, wherein the otic application is configured for use in an ear of a human or animal subject for preventing, reducing, or treating upper respiratory infections such as SARS-COV-2.

In some aspects, the techniques described herein relate to an otic application, including at least one carrier medium and at least one drug having cytoprotective activity, wherein the otic application is configured for use in an ear of a human or animal subject for preventing, reducing, or treating upper respiratory infections such as SARS-COV-2.

In some aspects, the techniques described herein relate to an otic application, including at least one carrier medium and at least one a drug component having anti-inflammatory activity, wherein the otic application is configured for use in an ear of a human or animal subject for preventing, reducing, or treating upper respiratory infections such as SARS-COV-2.

Methods of Treatment

In a further aspect, disclosed herein are methods of treatment. In certain embodiments, the first step of treatment of an upper respiratory infection is identifying the infection in a subject. This identification may be by self-identification, where the subject or professional compares the symptoms experienced by the subject to viral-associated clinical symptoms, such as those shown on Table 1. The infection may also be identified by use of an antigen test, a PCR test, a viral culture, or a serologic test. A high likelihood of infection could be identified through epidemiological evaluation of close contact with an infected individual.

In certain embodiments, a method of treatment may include administering a drug formulation to at least the ear of the subject, wherein the drug formulation comprises therapeutic compounds configured to treat the infection or relieve symptoms. The formulation may include a carrier medium and an antiviral agent. The formulation may reach an upper respiratory infection of the subject from the ear of the subject. By delivering the therapeutic compounds, such as an antiviral agent, from the point of administration at the ear of the subject to the upper respiratory system, the method can treat the upper respiratory infection at the site of infection. The therapeutic compounds may be transported from the ear to the upper respiratory system via the inner ear canal and the Eustachian tube. This transportation may be by means of diffusion.

In some embodiments, the formulation comprises at least one antiviral agent. Antiviral agents are compounds that interfere with the lifecycle of a virus, prevent its replication, or directly eliminate the virus, and may thereby reduce the severity and duration of viral infections and prevent their spread when the agents are present at the site of infection. Antiviral agents may work by inhibiting viral replication by blocking entry into host cells, blocking genome replication, or inhibiting the release of newly formed virus particles. Some antiviral agents interfere with viral enzymes essential for replication, while others physically destroy viral particles. In some embodiments, the antiviral agent comprises antiviral drug hemin, which inhibits a variety of infections via the induction of a host protective endogenous enzyme heme oxygenase-1 (HO-1). In some embodiments, the antiviral agent comprises remdesivir (RMD). RMD suppresses viral infections by a mechanism that involves targeting RNA-dependent polymerase which is an essential enzyme for viral replication. In some embodiments, the antiviral agent may be a protein, a peptide, a peptidomimetic, and/or a modified heparin. In some embodiments, the antiviral agent may treat upper respiratory infections of SARS-COV-2, the viral cause of a worldwide pandemic.

In some embodiments, the formulation comprises at least one heme oxygenase-1 (HO-1) modulator. In some embodiments, the at least one heme oxygenase-1 (HO-1) modulator comprises hemin, which causes induction of a host protective endogenous enzyme heme oxygenase-1 (HO-1).

In some embodiments, the formulation comprises at least one drug component having anti-inflammatory activity. In some embodiments, the at least one drug component having anti-inflammatory activity comprises corticosteroids, salicylates, and/or curcumin. In some embodiments, the drug component having anti-inflammatory may reduce inflammation of the upper respiratory system that results from viral infection.

In some embodiments, the formulation comprises at least one drug component having cytoprotective activity. In some embodiments, the at least one drug component having cytoprotective activity comprises hemin, a strong inducer of an endogenous cytoprotective enzyme heme oxygenase-1 (HO-1).

In some embodiments, the application comprises at least one carrier medium. In certain embodiments, small drug molecules are formulated in a carrier medium, preferably non-polar media (for example, oils or other drug carriers) with compatibility to the lipid-rich hydrophobic tympanic membrane that could promote translocation of drugs across the tympanic membrane via diffusion, active or passive transport, or permeation.

In some embodiments, the formulation is configured to transport across a tympanic membrane of the subject from the ear. This configuration may lead to a carrier medium of the correct polarity to transport the drug components and/or antiviral agents it carries. It may also lead to a carrier medium, drug components, and antiviral agents of sufficiently small size to transport across or permeate the porous tympanic membrane porous (about 100-150 μm).

In some embodiments, the drug formulation is administered several times. In one example embodiment, the drug formulation is administered to the subject's ear at least twice a day for three days. Testing by the inventors has shown that three day's application of therapeutic compounds reduced the infection and relieved its symptoms, according to certain embodiments. Repeated exposure to the therapeutic compounds in the drug formulation can increase the effects of fighting the infection in the upper respiratory system and/or relieving its symptoms.

In some embodiments, the drug formulation is heated to above room temperature. The inventors surprisingly discovered that higher temperatures increased the rate of transportation of essential oils used for testing from the ear to the upper respiratory system. Higher temperature may decrease the viscosity of the drug formulation and thereby increase its rate of movement through the ear canal. Higher temperature may also increase the vapor pressure of the drug formulation, and increase the rate of diffusion through the ear.

In some embodiments, a fragrant essential oil may be included in the carrier medium or in the drug formulation. Fragrant essential oils are widely held to have therapeutic properties to assist the ill subject. Further, essential oils may have a beneficial polarity for transporting other therapeutics as a carrier medium. Finally, fragrant essential oils may allow the subject to detect the arrival of the drug formulation from its application in the ear to the upper respiratory system when the characteristically-pleasing scents of the fragrant essential oils are detected in the nose, just above the nasopharynx where the Eustachian tube connects.

In some embodiments, the method includes applying a thermal, electrical or electromagnetic impulse, manual or mechanical muscle contraction or stimulation of muscles, nerves or tissues externally proximate to an eardrum to facilitate drug absorption and translocation of drugs across a tympanic membrane of the subject. For example, a thermal, electrical or electromagnetic impulse, manual or mechanical muscle contraction or stimulation of muscles, nerves or tissue may be applied on an external surface of the body, or on an internal surface of the body, for example within 6 inches, 5 inches, 4 inches, 3 inches, 2 inches, 1 inch or less away from an eardrum.

Physical interaction with the tissues of the inner ear can increase the rate of transportation of formulation through the tympanic membrane and through the Eustachian tube. The mechanism may be by inducing small movements in these small cavities of the head to accelerate transportation of drug formulation. In some example embodiments, a TENS device can be used to stimulate the inner ear by placing the TENS pads proximate to the eardrums and starting the electrical stimulation.

In some aspects, the techniques described herein relate to a method for treating upper respiratory infections in a human or animal subject, the method including: local administration of a drug formulation to an ear of a subject, the drug formulation including: at least one carrier medium; at least one antiviral agent; at least one heme oxygenase-1 (HO-1) modulator; at least one drug component having anti-inflammatory activity; and at least one drug component having cytoprotective activity.

In some aspects, the techniques described herein relate to a method for treating upper respiratory infection, the method including: administering of a drug formulation to at least an ear of a subject, wherein the drug formulation includes: at least one carrier medium; at least one antiviral agent; at least one heme oxygenase-1 (HO-1) modulator; at least one drug component having anti-inflammatory activity; and at least one drug component having cytoprotective activity; applying thermal, electrical or electromagnetic impulse, manual or mechanical muscle contraction or stimulation of muscles, nerves or tissues externally proximate to an eardrum to facilitate drug absorption and translocation of drugs across a tympanic membrane of the subject.

EXAMPLES

Some aspects of the embodiments discussed above are disclosed in further detail in the following examples, which are not in any way intended to limit the scope of the present disclosure. Those in the art will appreciate that many other embodiments also fall within the scope of the disclosure, as it is described herein above and in the claims.

Example 1

To test the hypothesis that these oils could transport through the tympanic membrane to the upper respiratory system, one of the inventors, hereafter referred to as "the subject" used Jojoba oil, as a representative example for other oils, spiked with eucalyptus oil (other oils, combinations of oils or other drug carriers may be used) and placed in his ears. Interestingly, within about 10 minutes, the subject felt eucalyptus olfaction in the nose and back of the throat the intensity of which increased with time, indicating translocation of the oil content across the tympanic membrane.

FIG. 2 depicts line graphs illustrating the results of further tests of transcutaneous electrical nerve stimulation (TENS) device usage and liquid otic application temperature on carrier oil permeation across the tymphanic membrane, according to certain embodiments. In other words, FIG. 2 Graph A shows testing of permeation of oil used as a drug carrier across the tympanic membrane. The scent from a fragrant essential oil mixture placed applied in the ear diffused through the ear canal, passed through the tympanic membrane and the eustachian tube, then registered as a strong scent as it reached the olifactory tissue in the upper part of the nasal cavity. Because the oil placed int the ear registered as a strong scent in the nasal cavity, it demonstrated that the oil permeated through the tympanic membrane.

In Graph A of FIG. 2, the individual testing the effect recorded the relative intensity of eucalyptus olefaction as measured over time after a mixture of Jojoba oil spiked with eucalyptus oil was placed into the ear canal. In this graph, higher relative units correspond to a more intense scent of at the time marked. The line marked with black dots depicts the olefaction intensity increasingly slowly over time after applying the essential oil mixture at about room temperature, 25° C. The inventors surprisingly found that heating the essential oil mixture to 40° C. before application greatly increased the intensity of eucalyptus olfaction, as depicted with the line marked by white squares. Administration of the oil formulation warmed to about 40° C., slightly above the physiological temperature 37° C., decreased the time of eucalyptus olfaction to less than about 5 minutes (FIG. 2 Graph A) with a greater intensity of the olfaction. The results of these tests indicate that a higher temperature of liquid otic application may increase the rate of transport rate of the carrier medium and any therapeutic in the mixture from the ear canal to the upper respiratory system.

Example 2

The inventors of the present application surprisingly discovered through further testing that the use of a TENS device increased the trans-tympanic membrane transport. Graph B of FIG. 2 illustrates the recorded olfaction intensity of eucalyptus oil in the nose and throat after placing a tincture of Jojoba oil spiked with eucalyptus oil in the ear canal, and then placing pads of a battery-operated TENS device externally proximate to the eardrum with a regulated electric impulse. Even at a low electric impulse, the intensity of eucalyptus olfaction was surprisingly far greater in the nose and back of the throat and more rapid than that without the TENS device, indicating increased translocation of the oil content across tympanic membrane (or eardrum). Thus, electric impulse or mechanical agitation and warming up of eucalyptus-spiked oil that markedly facilitated the intensity of eucalyptus olfaction across the tympanic membrane in less than 2 minutes (FIG. 2 Graph B). The inventors of the present disclosure do not know the exact mechanism of this strange phenomenon; however, production of electrical impulse by TENS proximate to the tympanic membrane might be a likely cause, among other factors. Another aspect of this disclosure presents thermal, physical stimulation of the nerves and muscle tissues by gentle manual, electrical or vibrations created by TENS or other higher intensity electromagnetic energy producing devices for strong muscle contractions proximate to the tympanic membrane (or eardrum) to improve trans-tympanic membrane drug delivery.

Example 3

To test whether a drug molecule that would inhibit the replication of all thus far reported viral strains of SARS-COV-2, including the newly identify XBB and XBB1.5 strains, the inventors of this disclosure chose a small molecule, hemin, and RMD as representative drug molecules and tested their effect on the infection of SARS-COV-2, in vitro. All in vitro infectivity and drug testing against SARS-COV-2 disclosed herein were performed in a BSL-3 laboratory at a contracted laboratory. An account of the observations from these experiments is described as follows.

FIG. 3 shows the effect of an antiviral drug, hemin, on the infectivity of SARS-COV-2 to epithelial cells expressing ACE-2 and TMPRSS-2, the cell surface receptors to which the virus binds to gain cellular entry. Cells were treated with hemin at various concentrations followed by infection with a live Omicron strain of SARS-COV-2 for 3 days. Virus levels were quantified by determining the virus-NP protein levels in the culture media. Data are presented from cells infected with SARS-COV-2 at a multiplication of infection (MOI) of 0.001 and 0.01.

Figure 4:
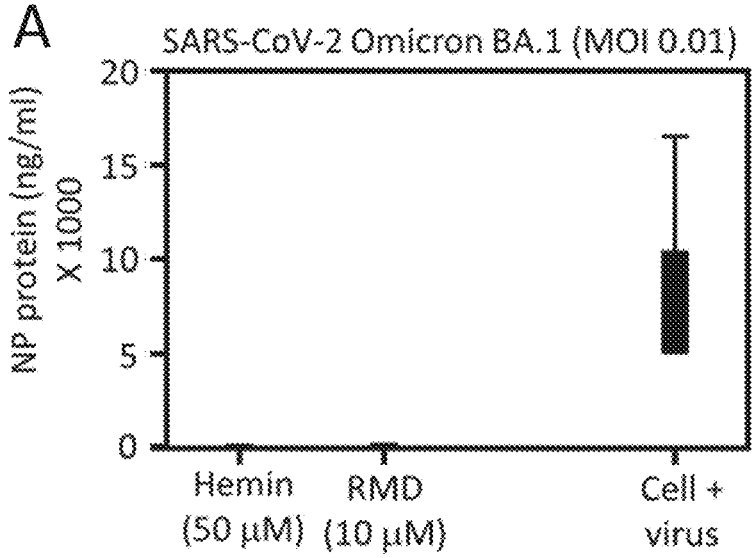
FIG. 4 depicts box-and-whiskers plots illustrating the effect of antiviral drugs, hemin and remdesivir (RMD), on the infectivity of cells by Omicron strains BA.1 (panel A), BA.2 (panel B) and BA.5 (panel C) at an MOI of 0.01 as described in legends to FIG. 3. Virus levels were quantified by determining the virus-NP protein levels in the culture media.
Figure 4:
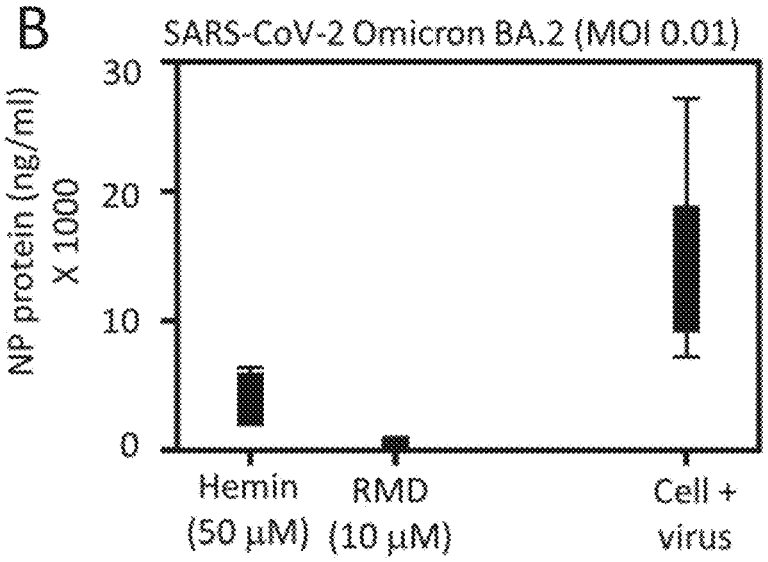
Figure 4:
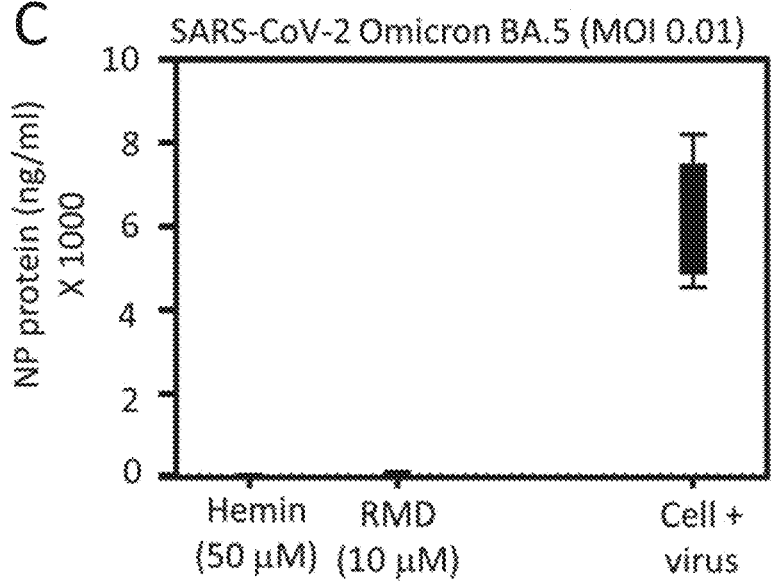
Figure 5:
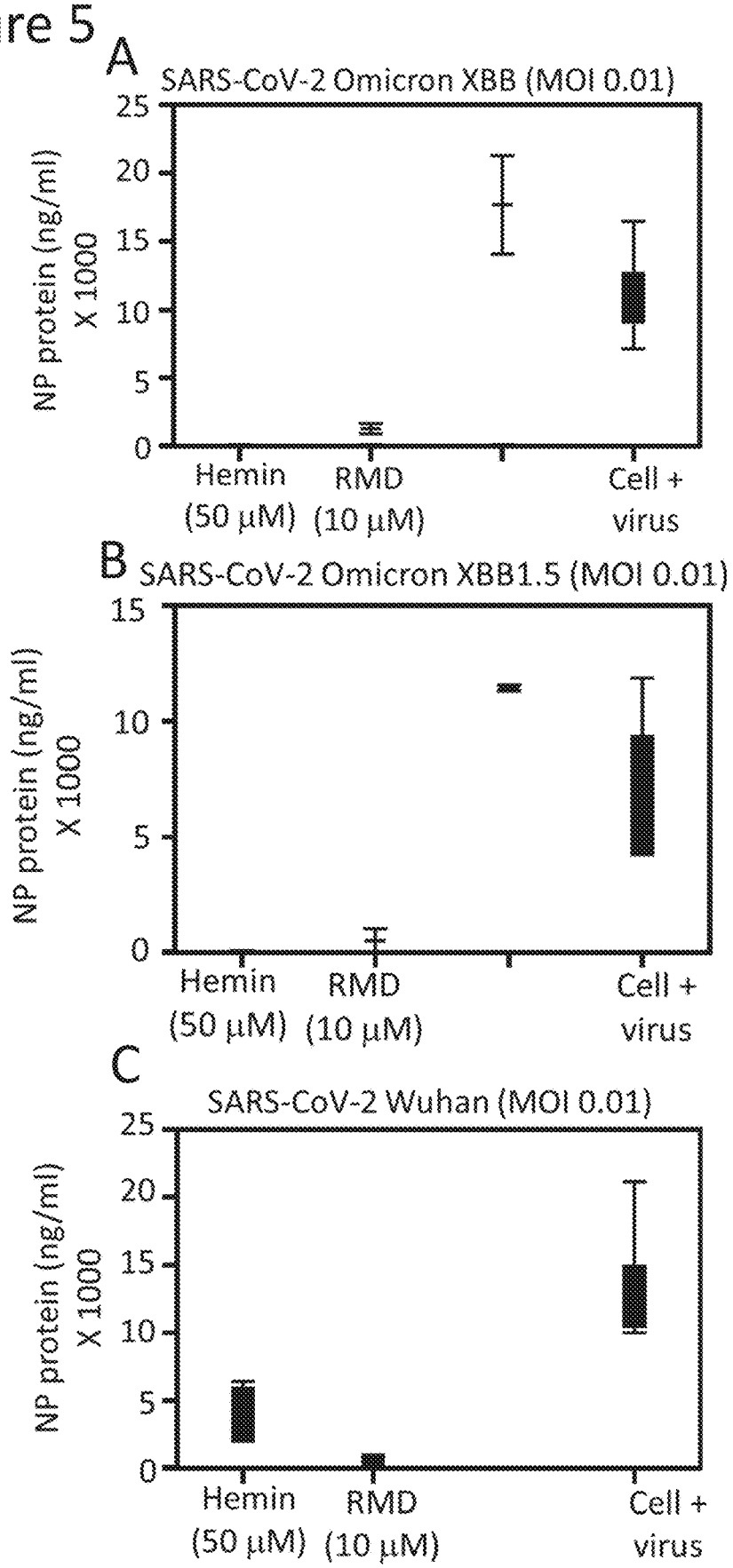
FIG. 5 depicts box-and-whiskers plots illustrating the effect of antiviral drugs, hemin and remdesivir (RMD), on the infectivity of cells by new Omicron strains XBB (panel A), XBB1.5 (panel B) and the original Wuhan SARS-COV-2 strain (panel C) at an MOI of 0.01 as described in legends to FIG. 3. Virus levels were quantified by determining the virus-NP protein levels in the culture media.

In multiple replicate in vitro experiments disclosed in this disclosure both hemin and RMD were found to remarkably inhibit cellular infection by SARS-COV-2. FIG. 3 displays a dose-dependent inhibition of hemin on SARS-COV-2 BA.1. Whether hemin and RMD provide cellular protection against SARS-COV-2 mutant variants was also tested, and the findings are in this disclosure. Amazingly, both hemin and RMD not only protected cells against SARS-COV-2 BA.1 infection, but also significantly suppressed replication of multiple SARS-COV-2 variants, including BA.2, BA.5 as shown in FIG. 4, and also the current mutant variants of interest XBB, XBB1.5 (FIG. 5). Both antivirals markedly suppressed SARS-COV-2 infection against the original WA1 viral strain as well (FIG. 5, panel C).

FIG. 4 displays the effect of antiviral drugs, hemin and remdesivir (RMD), on the infectivity of cells by Omicron strains BA.1 (panel A), BA.2 (panel B) and BA.5 (panel C) at an MOI of 0.01 as described in legends to FIG. 3. Virus levels were quantified by determining the virus-NP protein levels in the culture media.

FIG. 5 displays the effect of antiviral drugs, hemin and remdesivir (RMD), on the infectivity of cells by new Omicron strains XBB (panel A), XBB1.5 (panel B) and the original Wuhan SARS-COV-2 strain (panel C) at an MOI of 0.01 as described in legends to FIG. 3. Virus levels were quantified by determining the virus-NP protein levels in the culture media.

These data strongly suggest a broad utility of HO-1 inducing agents and antiviral drugs against SARS-COV-2, alone or in combination, in the treatment of viral infections regardless of the type of viruses or their mutant variants. Antiviral drug RMD is currently being used to treat COVID patients; however, by intravenous administration. Notably, in general, a vaccine produced against one particular viral strain is not protective against infections with most other respiratory viral mutants or variants. Therefore, in addition to vaccines, therapeutic modality consisting of one or more antiviral agents administered in the car of a subject provide an effective protection against respiratory viral infections.

Example 4

Despite receiving the updated influenza, RSV and COVID-19 booster vaccines, one of the inventors developed symptoms reminiscent of any cold or viral infection, including fever above 100° F., body-ache, headache, loss of appetite, fatigue, and ear pain. The inventor tested positive for COVID-19 on an FDA-approved home test kit twice and confirmed positive reactivity on the test strip suggestive of an early phase of SARS-COV-2 infection. The tests were performed strictly following the instructions on the package insert.

Thereafter, it was helpful to know if antiviral agents administered in the outer ear of a subject, tested positive for COVID-19, could diffuse or transport through the ear canal to the primary infection sites in the upper respiratory system and effectively suppress viral infection and relieve symptoms. To test this question, the COVID-19-positive subject placed a few drops of eucalyptus-spiked Jojoba oil containing an antiviral drug hemin, pre-warmed to 40° C., in his cars twice-a-day for 3 days and tested for COVID-19 antigen in the nasal swab specimens on an FDA-approved COVID-19 home test kit, and continued to monitor virus-associated symptoms regularly. The observations from these tests were remarkable. The parameters listed in Table 1 show that drug administered to the outer ear canal of a COVID-19-positive subject substantially inhibited COVID-19 infection and also reduced virus-associated symptoms in 3 to 7 days. Table 1 lists several viral-associated clinical symptoms that were relieved or reduced by certain embodiments.

TABLE 1

Parameters after drug placement in the ear of a COVID-19-positive subject

| | Symptoms | | |
| --- | --- | --- | --- |
| Parameters | Oil with antiviral agent (on day 0) | Oil with antiviral agent (on day 3) | Oil with antiviral agent (on day 7) |
| COVID-19 Antigen Home Test Kit | Low positive | Negative | Negative |
| Fever | 103° F. | 100° F. | 98° F. |
| Fatigue | Yes | Yes | Yes |
| Nausea | Yes | No | No |
| Dry cough | Yes | Yes | No |
| Muscle ache | Yes | Yes | Yes |
| Loss of appetite | Yes | Yes | Yes |
| Headache | Yes | No | No |
| Pain in the ear | Yes | No | No |
| Abdominal pain | Yes | Yes | No |

These data provide evidence that intra-ear administration of small molecules exhibiting antiviral, anti-inflammatory and/or cytoprotective activities formulated in a proper drug carrier could deliver drugs directly to the primary infection sites for treating upper respiratory infections.

Example 5

A human or animal subject is afflicted with an upper respiratory infection. A liquid otic application is obtained which is made of a beneficial mixture of active ingredients, such as an antiviral agent, an HO-1 modulator, a drug having anti-inflammatory activity, and/or a drug having cytoprotective activity, together with a carrier medium. The liquid otic application is applied to the ear canal of the subject. The liquid otic application is allowed to remain in the ear canal for a time. The carrier medium diffuses or otherwise transports through the tympanic membrane and then through the Eustachian tube to the upper respiratory system of the subject, transporting along the beneficial mixture of active ingredients. Therefore, the beneficial mixture of active ingredients diffuse onto the tissues of the upper respiratory system, including the nasal cavity, the nasopharynx, the oropharynx, and laryngopharynx of the subject. The beneficial mixture of active ingredients provide protection to the cells of the subject's upper respiratory system, reduce the rate of viral replication there, and relieve symptoms caused by the infection.

OTHER CONSIDERATIONS

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," "involving," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Disjunctive language such as the phrase "at least one of X, Y or Z," unless specifically stated otherwise, is otherwise understood with the context as used in general to present that an item, term, etc., may be either X. Y or Z, or any combination thereof (such as X. Y and/or Z). Thus, such disjunctive language is not generally intended to, and should not, imply that certain embodiments require at least one of X, at least one of Y or at least one of Z to each be present.

The terms "about" or "approximate" and the like are synonymous and are used to indicate that the value modified by the term has an understood range associated with it, where the range can be ±20%, ±15%, ±10%, ±5%, or ±1%. The term "substantially" is used to indicate that a result (such as a measurement value) is close to a targeted value, where close can mean, for example, the result is within 80% of the value, within 90% of the value, within 95% of the value, or within 99% of the value.

Unless otherwise explicitly stated, articles such as "a" or "an" should generally be interpreted to include one or more described items.

While the above detailed description has shown, described, and pointed out novel features as applied to illustrative embodiments, it will be understood that various omissions, substitutions, and changes in the form and details of the devices or algorithms illustrated can be made without departing from the spirit of the disclosure. As will be recognized, certain embodiments described herein can be embodied within a form that does not provide all of the features and benefits set forth herein, as some features can be used or practiced separately from others. All changes which come within the meaning and range of equivalency of the claims are to be embraced within their scope.

It should be appreciated that all combinations of the foregoing concepts (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

The scope of the present disclosure is not intended to be limited by the specific disclosures of examples in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. An otic application for treatment of an upper respiratory infection, the otic application consisting of:
    a mixture of Jojoba oil and eucalyptus oil; and
    at least one antiviral agent selected from the group consisting of hemin, remdesivir, and a combination thereof;
    wherein the otic application is configured for use in an ear of a human or animal subject for reducing or treating upper respiratory infection; and
    wherein the otic application is configured to diffuse through an intact tympanic membrane of the subject from the ear and deliver the antiviral agent to the upper respiratory system, thereby reducing or treating the upper respiratory infection.

2. The otic application of claim 1, wherein the upper respiratory infection is SARS-COV-2.

3. The otic application of claim 1, wherein the otic application is liquid.

4. A method for treating upper respiratory infections in a human or animal subject, the method comprising:
    identifying a subject having an upper respiratory infection, and
    administering a drug formulation to an ear of the subject, the drug formulation consisting of:
        a mixture of Jojoba oil and eucalyptus oil; and
        at least one antiviral agent selected from the group consisting of hemin, remdesivir, and a combination thereof.

5. The method of claim 4, wherein the upper respiratory infection is SARS-COV-2.

6. The method of claim 4, wherein the method further comprises using a scent of the eucalyptus oil by olfactory tissues of the subject to detect whether the drug formulation has been delivered into an upper respiratory system of the subject.

7. The method of claim 4, wherein the administering of the drug formulation to at least the ear of the subject is repeated at least twice a day for three days.

8. The method of claim 4, wherein the drug formulation is applied at room temperature.

9. The method of claim 4, wherein the drug formulation is warmed above room temperature.

10. The method of claim 4, further comprising applying a thermal, electrical or electromagnetic impulse, manual or mechanical muscle contraction or stimulation of muscles, nerves or tissues externally proximate to an eardrum to facilitate drug absorption and translocation of drugs across a tympanic membrane of the subject.

11. The method of claim 10, wherein transcutaneous electrical nerve stimulation is applied externally within 6 inches from the eardrum.

12. An otic application for treatment of an upper respiratory infection, the otic application consisting of:
    a mixture of Jojoba oil and eucalyptus oil; and
    wherein the otic application is configured for use in an ear of a human or animal subject for reducing or treating upper respiratory infection; and
    wherein the otic application is configured to diffuse through an intact tympanic membrane of the subject from the ear and deliver the hemin to the upper respiratory system, thereby reducing or treating the upper respiratory infection.

13. The otic application of claim 12, wherein the upper respiratory infection is SARS-COV-2.

14. The otic application of claim 12, wherein the otic application is liquid.

15. The otic application of claim 12, wherein the otic application has a temperature of about 40° C.

16. The otic application of claim 1, wherein the antiviral agent is remdesivir.

17. The otic application of claim 1, wherein the antiviral agent is a combination of hemin and remdesivir.

18. The otic application of claim 1, wherein the otic application has a temperature of about 40° C.

* * * * *